(12) United States Patent
Ogino et al.

(10) Patent No.: US 6,885,964 B2
(45) Date of Patent: Apr. 26, 2005

(54) METHOD AND APPARATUS FOR THERMAL ANALYSIS

(75) Inventors: Takashi Ogino, Saitama (JP); Hirotaka Murakami, Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 57 days.

(21) Appl. No.: 10/202,884

(22) Filed: Jul. 26, 2002

(65) Prior Publication Data

US 2003/0060999 A1 Mar. 27, 2003

(30) Foreign Application Priority Data

Aug. 2, 2001  (JP) ........................................ 2001-235556

(51) Int. Cl.$^7$ ............................................... G01K 13/00
(52) U.S. Cl. ..................... 702/130; 702/132; 702/134; 702/136; 700/300; 374/11; 374/14; 374/144
(58) Field of Search ................................ 702/130, 132, 702/134, 136; 700/300, 121, 299; 374/11–15, 14, 10, 22, 24, 144

(56) References Cited

U.S. PATENT DOCUMENTS

| | | | | |
|---|---|---|---|---|
| 5,202,843 A | | 4/1993 | Kunimine et al. ............ | 703/6 |
| 5,931,140 A | * | 8/1999 | Maloney ..................... | 123/480 |
| 5,972,829 A | * | 10/1999 | Ichimura .................... | 502/303 |
| 6,275,750 B1 | * | 8/2001 | Uchida et al. .............. | 700/300 |

FOREIGN PATENT DOCUMENTS

JP           11-118740 A        4/1999

OTHER PUBLICATIONS

"A Two–Dimensional Finite Difference Program for Thermal Analysis of Rocket Thrust Chambers", NASA, Huntsfield, US, Sep. 1987, pp. 1–52.
XP–002281446, JP 06 218414 A (Nisshin Steel Co Ltd), Aug. 09, 1994, Derwent Publications Ltd..

* cited by examiner

*Primary Examiner*—John Barlow
*Assistant Examiner*—Hien Vo
(74) *Attorney, Agent, or Firm*—Birch, Stewart, Kolasch & Birch, LLP

(57) ABSTRACT

In a method and an apparatus for thermal analysis, a target region is divided by dividing the geometry of the target object of the thermal analysis into a finite number of finite elements or cells. The thermal analysis on the target region is conducted using the results of the division. A temperature distribution on the target object is obtained from the heat transfer coefficients by a temperature distribution calculating unit. The actual temperatures at specific points are obtained based on temperature distribution obtained by the specific point temperature calculating unit. Differences between the actually obtained temperatures at the specific points and the predetermined target temperatures at the specific points are obtained by a difference calculating/ determining unit. If the differences are determined to be out of the prescribed range, the heat transfer coefficients are changed by a heat transfer coefficient updating unit. These steps are repeated until the differences fall within the prescribed range so that temperature distribution on the target object is obtained. The method and apparatus for thermal analysis obtains temperature distribution universally, irrespective of geometries of the target object.

12 Claims, 10 Drawing Sheets

METHOD AND APPARATUS FOR THERMAL ANALYSIS

CROSS-REFERENCES TO RELATED APPLICATIONS

This nonprovisional application claims priority under 35 U.S.C. § 119(a) on Patent Application No. 2001-235556 filed in Japan on Aug. 2, 2001, the entirety of which is herein incorporated by reference.

BACKGROUND OF THE INVENTION

1. Field of the Invention

The present invention relates to a method and an apparatus that can be utilized for thermal analysis, e.g., for analyzing temperature distribution across a piston in an internal combustion engine, and more specifically, to a method and an apparatus for thermal analysis using a response surface method.

2. Description of the Background Art

When performing thermal analysis, e.g., as shown in Japanese Patent Document JP-A-11-118740, the entire contents of which are hereby incorporated by reference, an experimental formula for calculating a heat transfer coefficient of a heat transfer boundary on which natural convection heat transfer occurs is automatically selected depending on various conditions. A temperature value on the heat transfer boundary assumed for determining the heat transfer coefficient is obtained automatically by repetitive calculation while keeping consistence with the temperature of the heat transfer boundary obtained by a measure such as finite element method (FEM), or finite difference method.

SUMMARY OF THE INVENTION

The present invention overcomes the shortcomings associated with the background art and achieves other advantages not realized by the background art. The present inventors have determined that the background art suffers from at least the following disadvantages.

In the case where the experimental formula for calculating the heat transfer coefficient of the heat transfer boundary on which natural convection heat transfer occurs is automatically selected according to various conditions as described above, there exists a problem in that a large number of repetitive calculations or iterations are necessary for selecting an experimental formula suitable for a geometrical model of the object. In addition, a large number of iterations are required for determining the heat transfer coefficient and both the operator and/or the related equipment require a significant amount of time and effort.

In addition, there also exists a problem in that an experimental formula is required for every geometric model of the target object to be analyzed. Therefore, even when selection of the experimental formula is automated, if minor portions of the object or model are modified, it is necessary to establish an experimental formula for each and every modification. In addition, a significant amount of time and resources are required to perform iterative calculations for determining the associated heat transfer coefficients.

An object of the present invention to provide a method and an apparatus for thermal analysis that provides accurate and universal temperature distribution irrespective of geometries of the target object or model.

One or more of these and other objects are accomplished by a method for thermal analysis having an execution process in which a target region on a target object is divided by dividing a geometric model of the target object of the thermal analysis into a finite number of finite elements or cells and then the thermal analysis is conducted on the target region using the results of the division of the target region, the execution process comprising the steps of obtaining a temperature distribution in the target object using heat transfer coefficients obtained at a plurality of positions on a surface of the target model that is divided into target regions in a first step; obtaining at least one temperature of a specific point in the target regions based on the previously obtained temperature distribution in a second step; calculating differences between the at least one temperature at the specific point and at least one corresponding and predetermined target temperatures at the specific point in a third step; determining if the calculated differences fall within a prescribed range in fourth step; and changing the heat transfer coefficients of the first step into updated heat transfer coefficients when the differences are determined to be outside of the prescribed range in a fifth step.

One or more of these and other objects are further accomplished by a thermal analysis apparatus for performing a thermal analysis process, the apparatus comprising means for dividing a target region on a target object by dividing a geometric model of the target object of the thermal analysis process into a finite number of finite elements or cells and conducting thermal analysis on the target region using the results of the division of the target region; means for obtaining a temperature distribution in the target object using first heat transfer coefficients obtained at a plurality of positions on a surface of the target model that is divided into target regions; means for obtaining at least one temperature of a specific point in the target regions based on the previously obtained temperature distribution; means for calculating differences between the at least one temperature at the specific point and at least one corresponding and predetermined target temperatures at the specific point; means for determining if the calculated differences fall within a prescribed range; and means for changing the first heat transfer coefficients into updated heat transfer coefficients when the differences are determined to be outside of the prescribed range.

One or more of these and other objects are further accomplished by a thermal analysis apparatus for performing a thermal analysis process, the apparatus comprising an input device; a geometric calculating unit, the geometric calculating unit including an FEM analysis process section for dividing a target region on a target object by dividing a geometric model of the target object of the thermal analysis process into a finite number of finite elements or cells and conducting thermal analysis on the target region using the results of the division of the target region; a temporary memory; a temperature distribution calculating unit for obtaining a temperature distribution in the target object using first heat transfer coefficients obtained at a plurality of positions on a surface of the target model that is divided into target regions; a specific point temperature calculating unit for obtaining at least one temperature of a specific point in the target regions based on the previously obtained temperature distribution; a comparative determining unit for calculating differences between the at least one temperature at the specific point and at least one corresponding and predetermined target temperatures at the specific point means for determining if the calculated differences fall within a prescribed range; and an automated, iterative solver, the automated iterative solver including a process for changing the first heat transfer coefficients into updated heat transfer coefficients when the differences are determined to be outside of the prescribed range.

With a method and apparatus for thermal analysis according to the present invention, temperature distribution on the target object is obtained by utilizing the heat transfer coefficients at a plurality of positions on the surface of the target geometry that is divided into regions. The temperatures at the specific points on the target geometry are obtained based on the obtained temperature distribution, differences between the actually obtained temperatures at the specific points and the predetermined target temperatures at the specific points are obtained. In addition, the differences falling within the prescribed range are evaluated. When the differences are determined to be out of the specific range, the heat transfer coefficients are changed, and the heat transfer coefficients for obtaining temperature distribution is updated into the changed heat transfer coefficients. These steps are repeated until the differences fall within the prescribed range.

According to the method and the apparatus for thermal analysis of the present invention, since the heat transfer coefficients are automatically obtained repeatedly by computation, it is not necessary to select the experimental formula, whereby temperature distribution and the heat transfer coefficient can effectively be obtained. In addition, since the heat transfer coefficients and temperature distributions can be obtained continuously, the final temperature distribution and the heat transfer coefficient are obtained almost simultaneously, whereby operating efficiency improves.

Temperature distribution can be obtained by utilizing the heat transfer coefficients obtained by working out the simultaneous formula of approximate expressions for heat transfer coefficient, not by the experimental formula. Therefore, the convergence in differences can be obtained at the earlier timing, and the number of iterations until the final heat transfer coefficient and temperature distribution are obtained may be reduced.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 11($b$) is a sectional view showing the measuring points in FIG. 11($a$).

DETAILED DESCRIPTION OF THE PREFERRED EMBODIMENTS

The present invention will hereinafter be described with reference to the accompanying drawings. Referring now to the embodiments, a method and an apparatus for thermal analysis according to the present invention will be described hereinafter.

Figure 1:
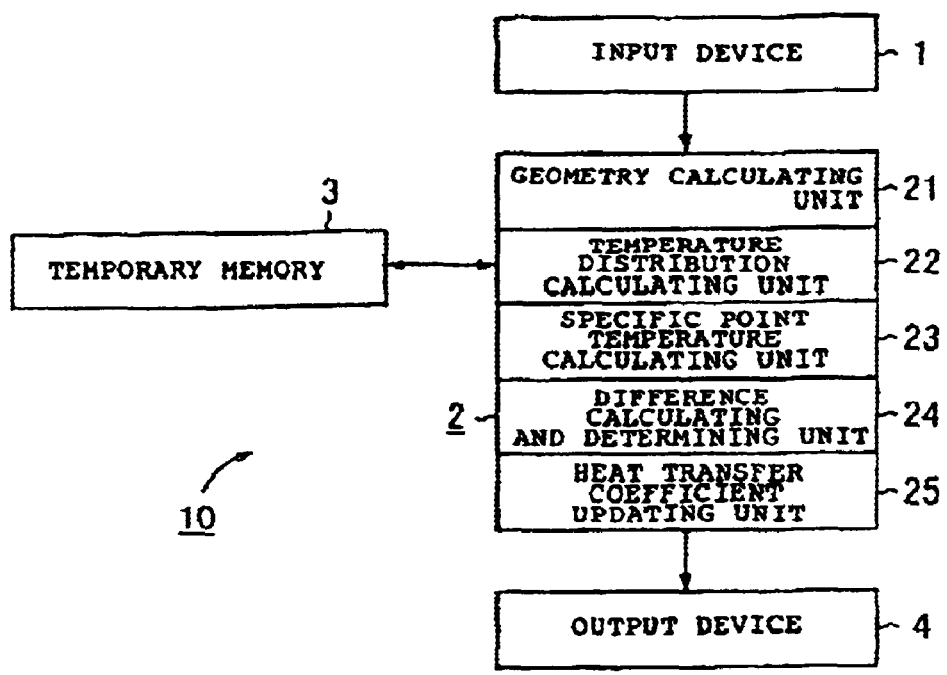
FIG. 1 is a block diagram of a thermal analysis apparatus according to one embodiment of the present invention.
Figure 2:
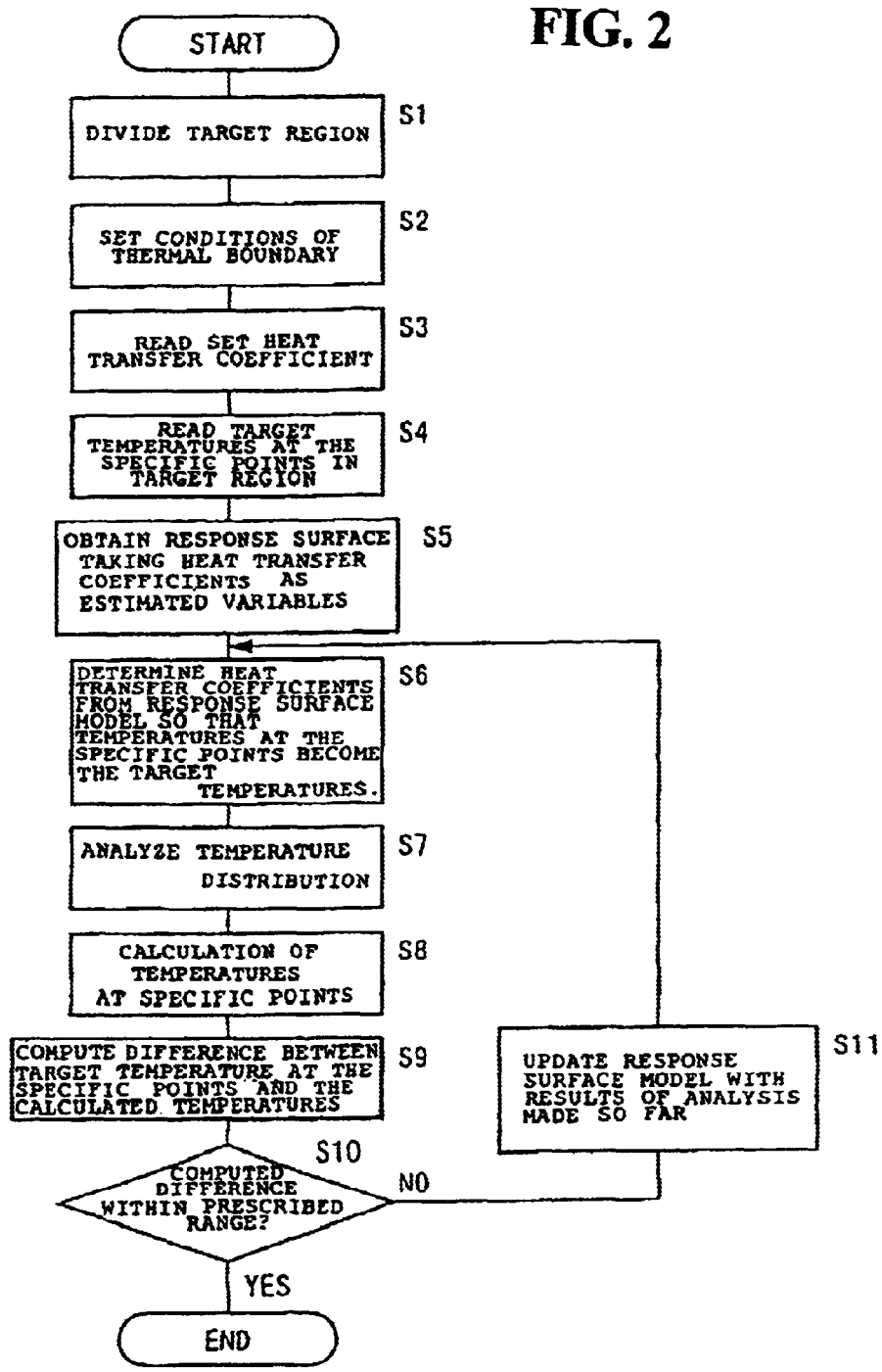
FIG. 2 is a flow chart describing a thermal analysis apparatus and method according to an embodiment of the present invention.
Figure 3:
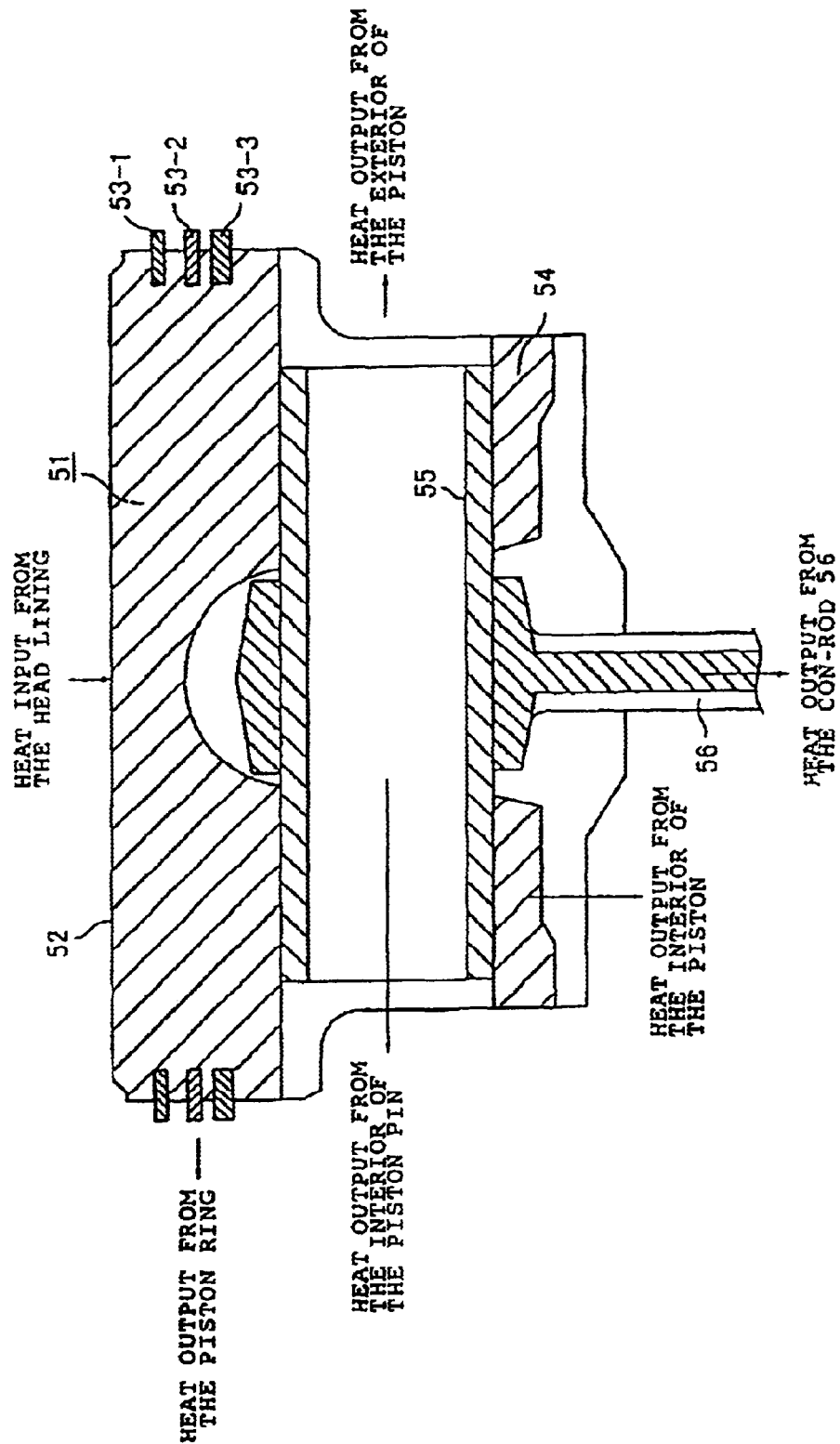
FIG. 3 is a cross sectional view of a piston to which the thermal analysis apparatus is applied according to an embodiment of the present invention.
Figure 4:
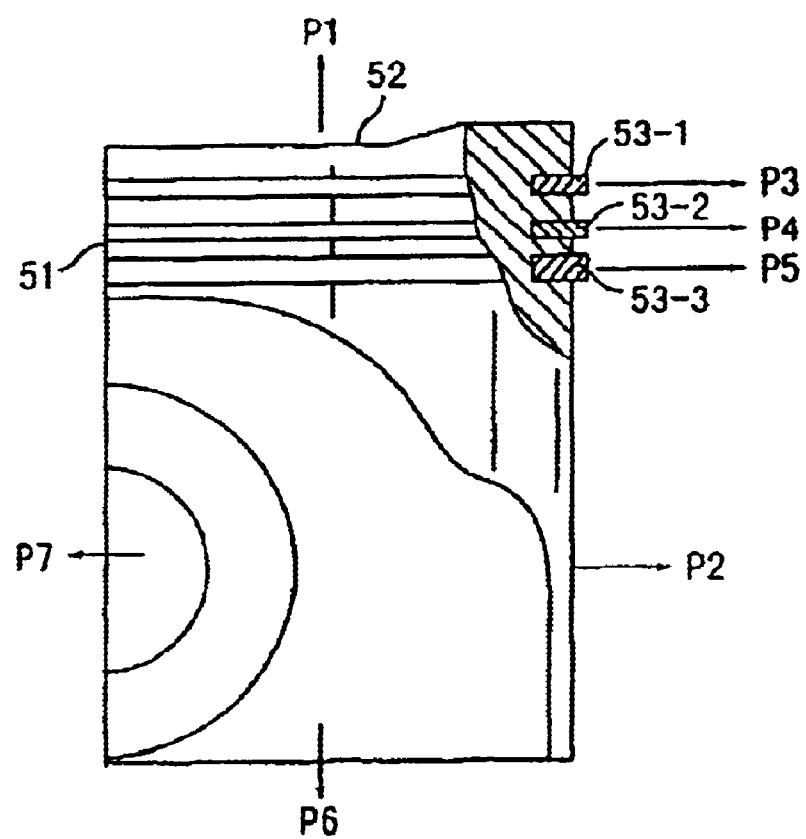
FIG. 4 is a partial cross sectional view showing heat transfer coefficients in the thermal analysis apparatus according to an embodiment of the present invention.
Figure 5:
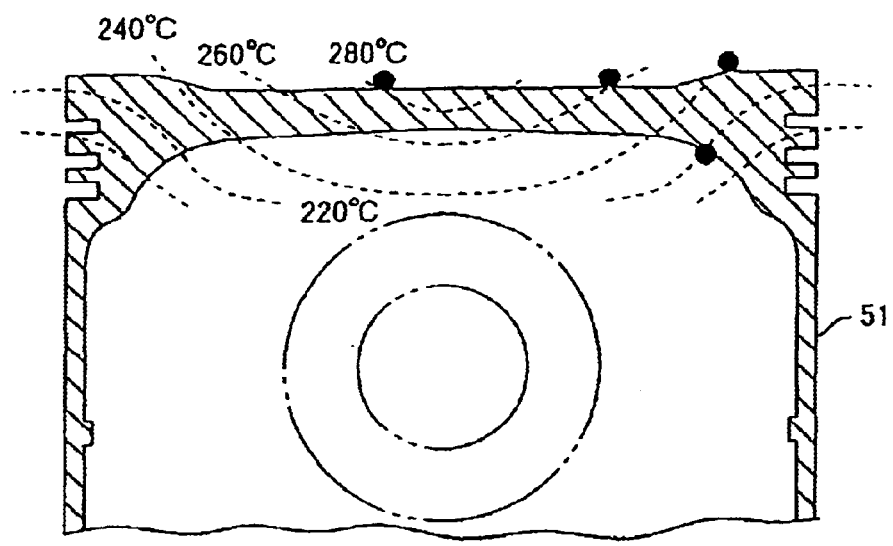
FIG. 5 is a sectional view showing temperature distributions obtained using the thermal analysis apparatus according to an embodiment of the present invention.
Figure 6:
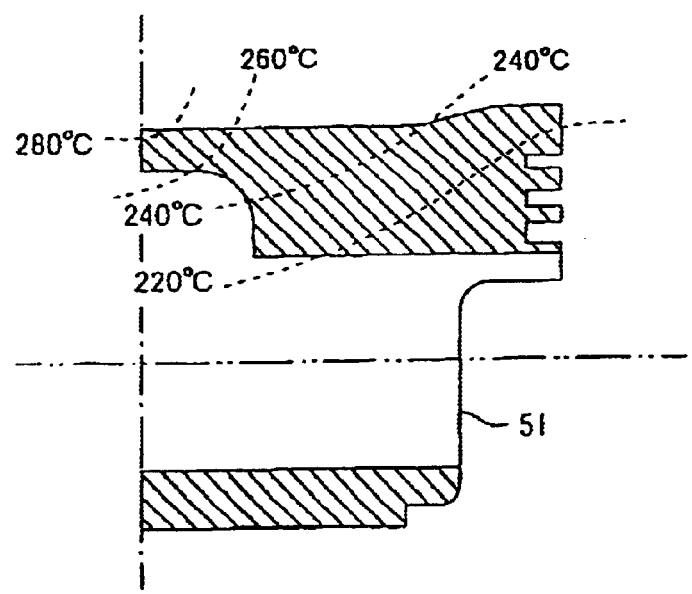
FIG. 6 is a partial, sectional view showing temperature distribution obtained using the thermal analysis apparatus according to an embodiment of the present invention.
Figure 7:
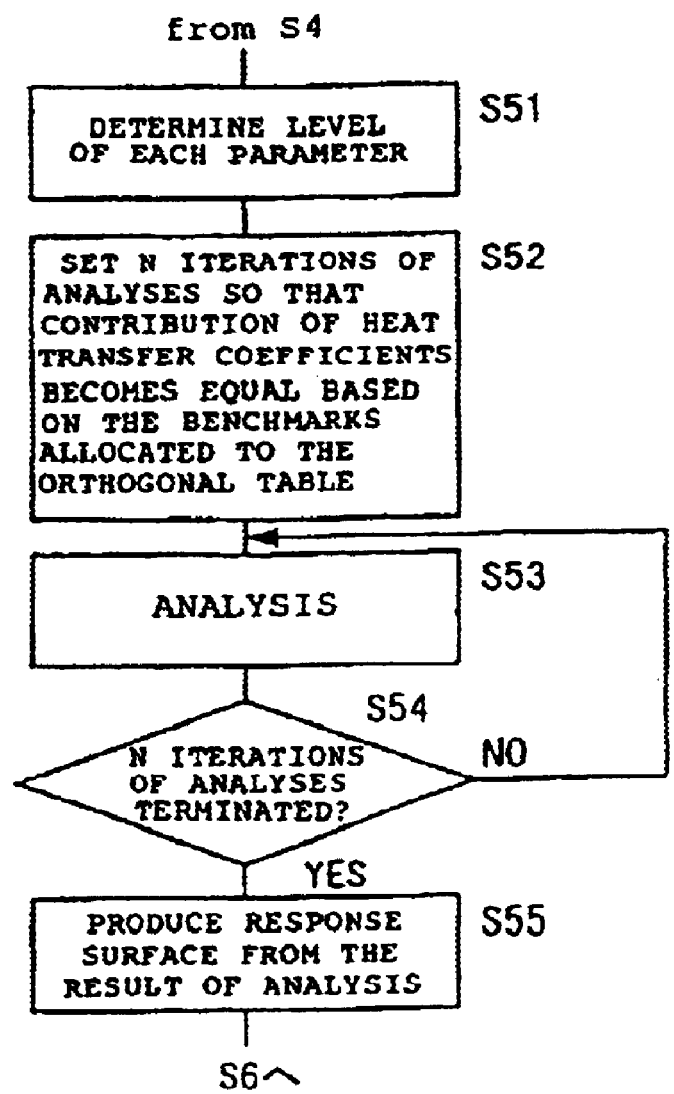
FIG. 7 is a flow chart for describing calculation of a thermal distribution in the thermal analysis apparatus according to an embodiment of the present invention.
Figure 8:
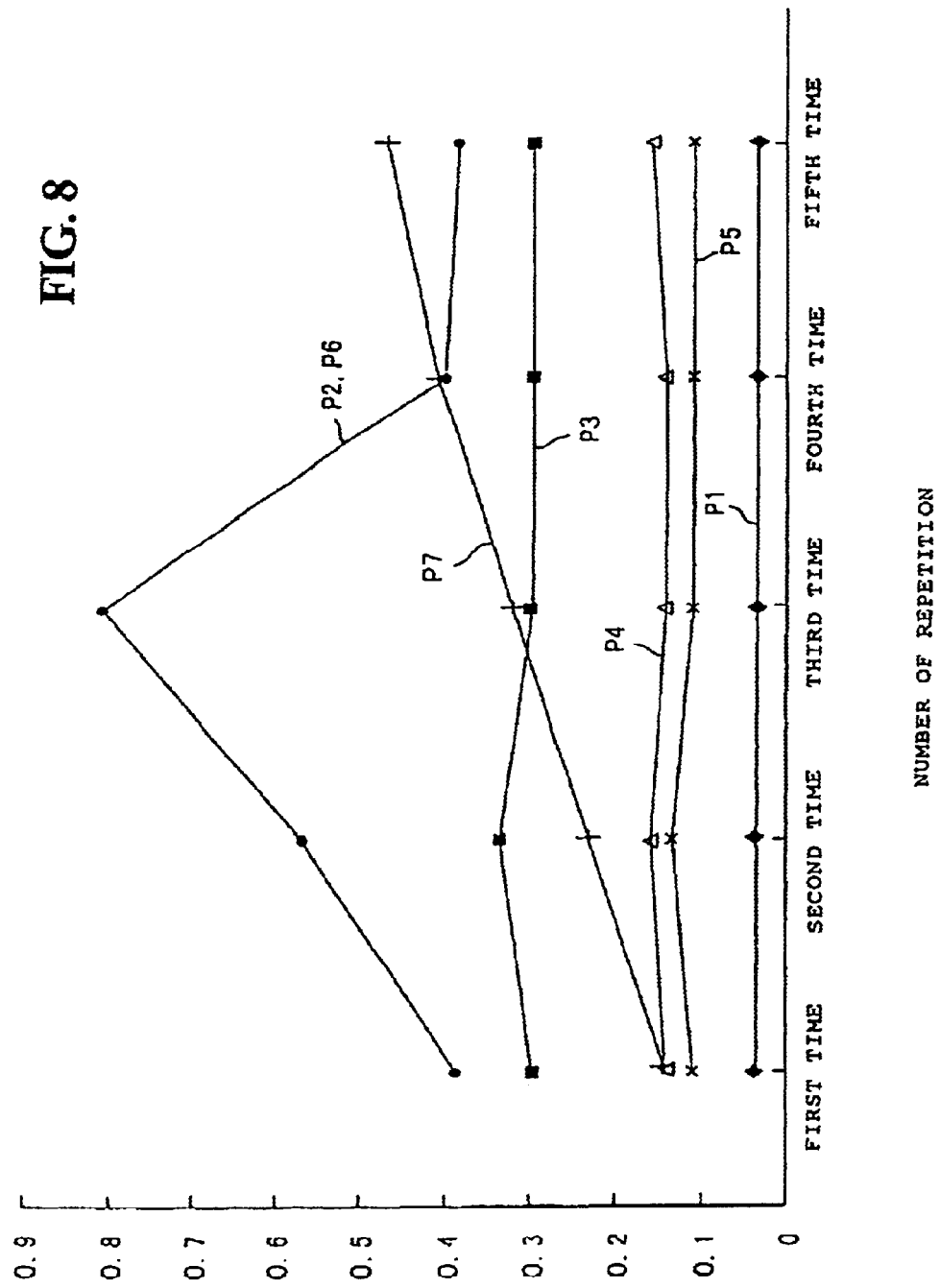
FIG. 8 is a graphical view showing a state in which a variation between the number of iterations and the heat transfer coefficients in the thermal analysis apparatus according to an embodiment of the present invention.
Figure 9:
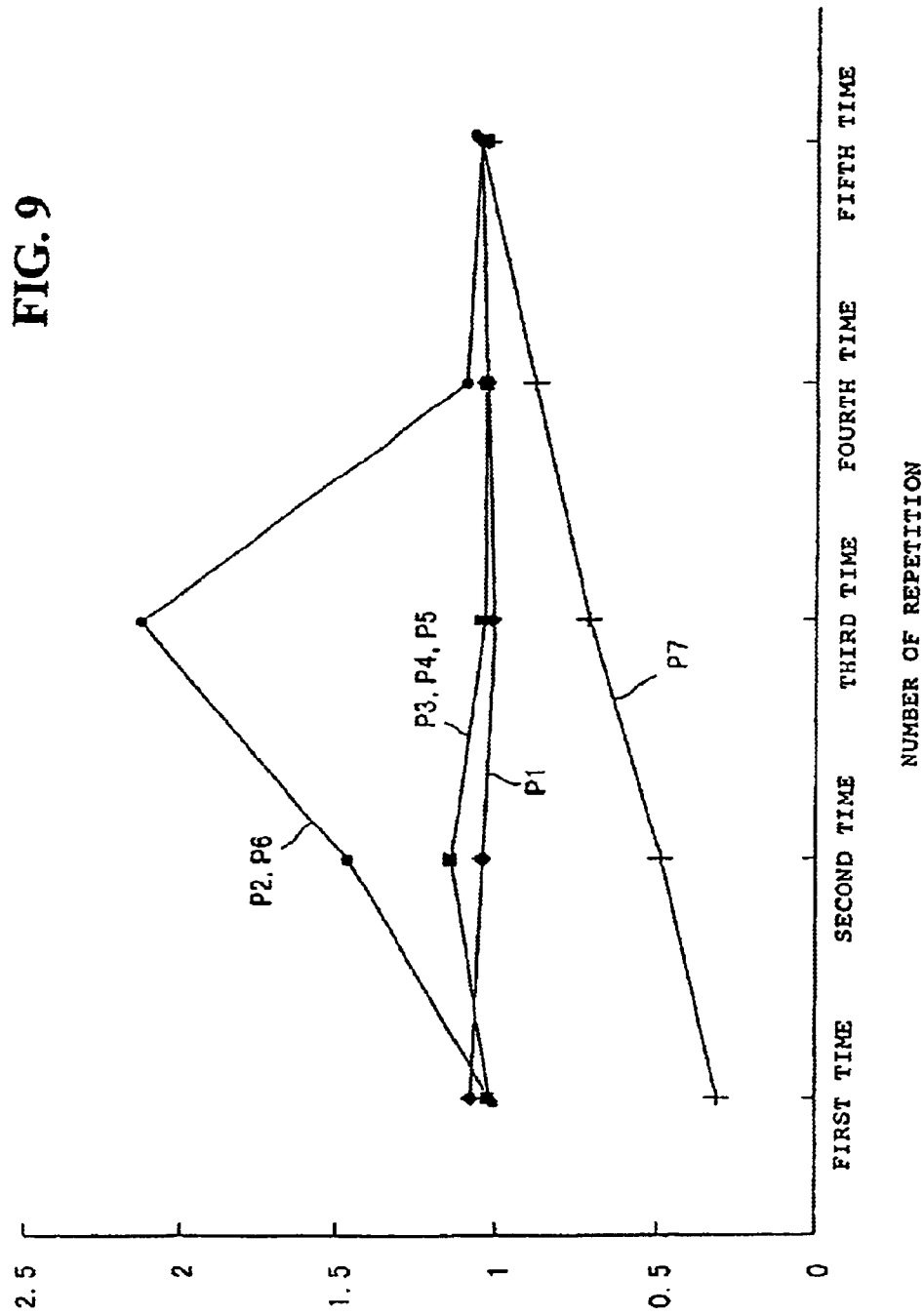
FIG. 9 is graphical view showing a state in which the relations between the numbers of iterations and the heat transfer coefficients are converging into a target value in the thermal analysis apparatus according to an embodiment of the present invention.
Figure 10:
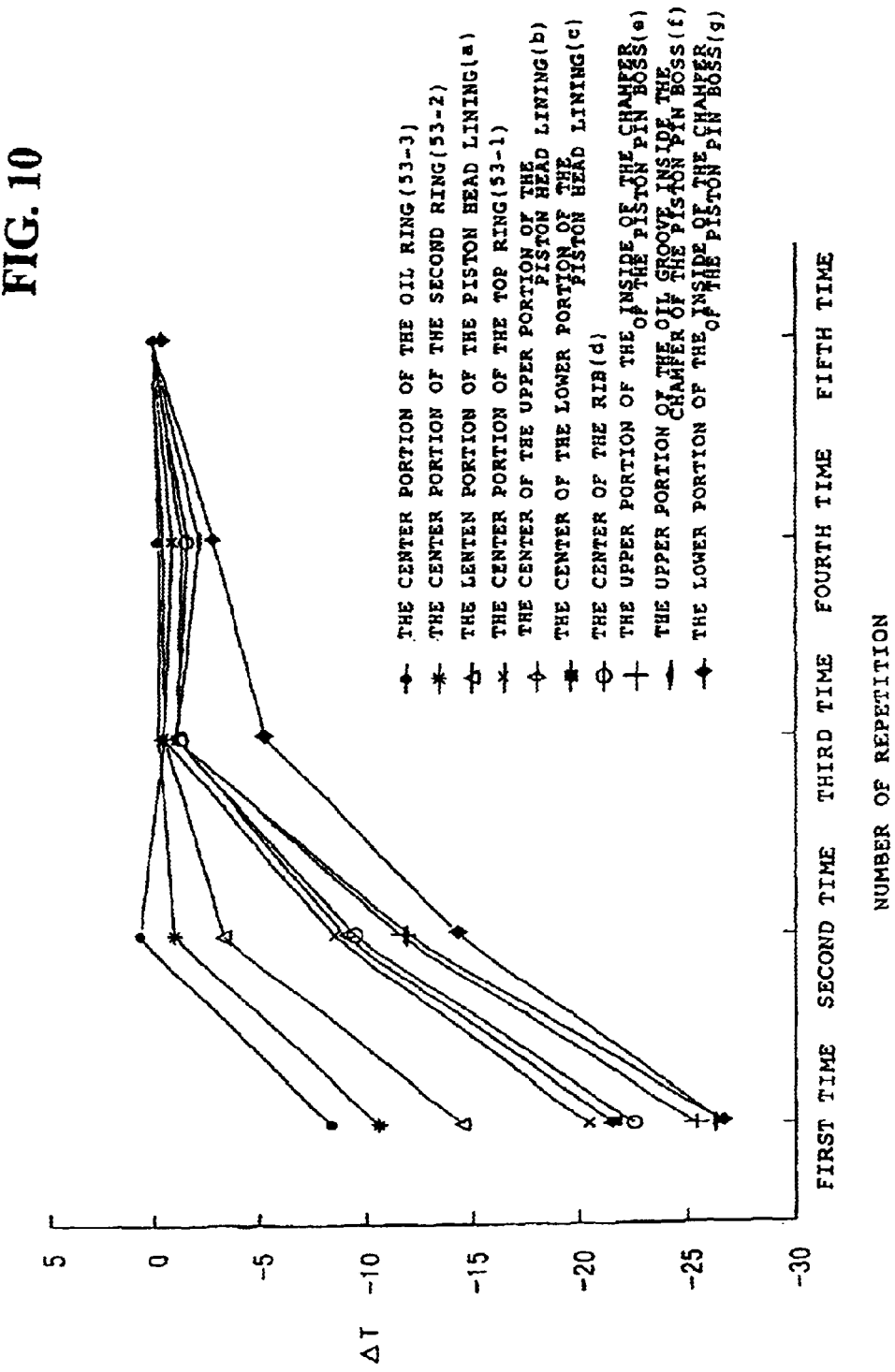
FIG. 10 is a graphical view showing a state in which the relations between the numbers of iterations and temperature differences are converging in the thermal analysis apparatus according to an embodiment of the present invention.
Figure 11A:
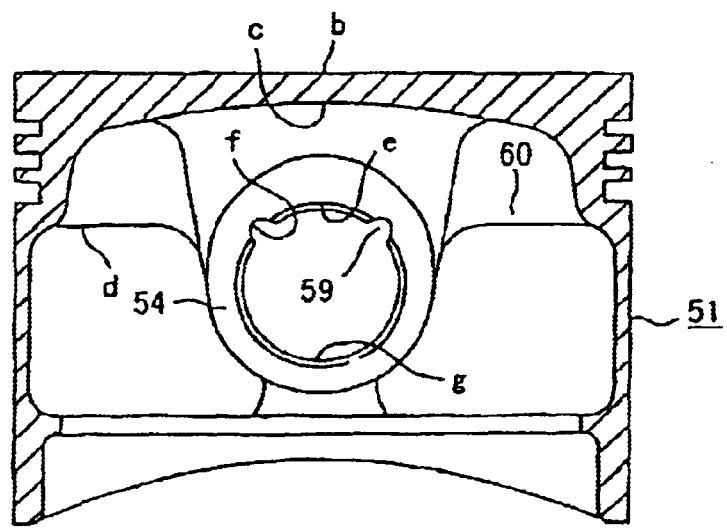
FIG. 11($a$) is a sectional view showing the measuring points in FIG. 10.
Figure 11B:
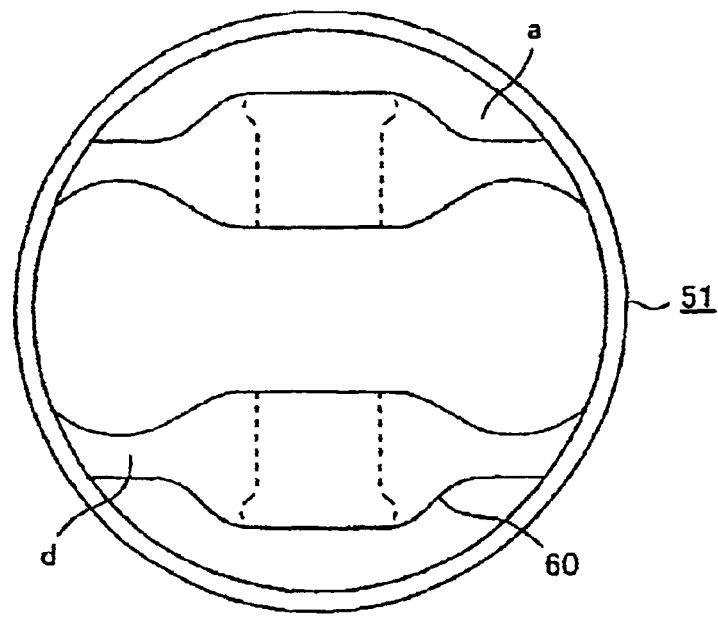

FIG. 1 is a block diagram of a thermal analysis apparatus according to one embodiment of the present invention. FIG. 2 is a flow chart describing a thermal analysis apparatus and method according to an embodiment of the present invention. FIG. 3 is a cross sectional view of a piston to which the thermal analysis apparatus is applied according to an embodiment of the present invention. FIG. 4 is a partial cross sectional view showing heat transfer coefficients in the thermal analysis apparatus according to an embodiment of the present invention. FIG. 5 is a sectional view showing temperature distributions obtained using the thermal analysis apparatus according to an embodiment of the present invention. FIG. 6 is a partial, sectional view showing temperature distribution obtained using the thermal analysis apparatus according to an embodiment of the present invention. FIG. 7 is a flow chart for describing calculation of a thermal distribution in the thermal analysis apparatus according to an embodiment of the present invention. FIG. 8 is a graphical view showing a state in which a variation between the number of iterations and the heat transfer coefficients in the thermal analysis apparatus according to an embodiment of the present invention. FIG. 9 is graphical view showing a state in which the relations between the numbers of iterations and the heat transfer coefficients are converging into a target value in the thermal analysis apparatus according to an embodiment of the present invention. FIG. 10 is a graphical view showing a state in which the relations between the numbers of iterations and temperature differences are converging in the thermal analysis apparatus according to an embodiment of the present invention. FIG. 11($a$) is a sectional view showing the measuring points in FIG. 10. FIG. 11(b) is a sectional view showing the measuring points in FIG. 11(a).

An exemplary case in which the thermal analysis apparatus 10 shown in FIG. 1 is applied to a piston in an internal combustion engine will be described in greater detail hereinafter. However, one of skill in the art will appreciate that the following method and apparatus can be applied to elements and equipment other than the piston shown in the accompanying figures. The thermal analysis apparatus 10 includes an input device 1, a ROM (not shown), a temporary memory 3 having a work area, a control unit 2 cooperating with the ROM and the temporary memory 3, and an output device 4.

Three-dimensional data on the piston, an initial value of the heat transfer coefficient, and the temperature at a predetermined specific point are entered through the input device 1. The control unit 2 operatively includes a geometry calculating unit 21 for producing a three dimensional model of the piston from three-dimensional data and performing division of a region of the three-dimensional model for FEM analysis. In addition, the control unit 2 includes a temperature distribution calculating unit 22 for determining temperature distribution of the piston using the heat transfer coefficients at a plurality of positions on the surface of the piston that is divided into regions, a specific point temperature calculating unit 23 for obtaining the temperature at the specific point in the target geometry of the piston from the obtained temperature distribution, a difference calculating/determining unit 24 for obtaining the difference between the actual obtained temperatures at the specific points and the temperatures at the specific points predetermined for the specific points. The difference calculating/determining unit then determines whether or not the obtained differences fall within the predetermined range.

A heat transfer coefficient updating unit 25 for varying the heat transfer coefficient when the difference is determined to be out of the prescribed range and repeating the procedure until the difference falls within the prescribed range. The changed heat transfer coefficient is used as a heat transfer coefficient in a temperature distribution calculating unit 22 that is also provided. More specifically, the temperature distribution calculating unit 22 performs heat distribution analysis including analysis of a response surface by FEM analysis. Previous to the description about the operation of the thermal analysis apparatus 10, an outline of the analysis system to which the thermal analysis apparatus 10 is applied will be described hereinafter.

A model of the piston, or other target object, is made, and the model is divided into mesh or cells for FEM analysis. Subsequently, various elements of the piston and conditions of calculation are entered, temperature distribution is analyzed, the strength against an explosive load, inertial force(s), heat stress(es), and the like are analyzed based on the result of temperature distribution analysis. The calculation of fatigue, verification of safety ratio, and the like are also performed as desired thereinafter.

The thermal analysis apparatus 10 is used in the aforementioned temperature distribution analysis. The reason for performing temperature distribution analysis here is as follows. Aluminum alloy material used for the piston that is to be exposed to temperatures as high as 300° C. or more is at risk for significant deterioration in strength due to the excessive temperatures. Therefore, by obtaining temperature distributions at the respective points of the piston in advance, verification of strength and verification of the stresses experienced by the piston can be made using a fatigue limit diagram in which the influence of heat caused by the combination of an explosive force and an inertial force is taken into consideration.

The operation of the thermal analysis apparatus 10 constructed as described above will be described based on the flow chart of FIG. 2. When a program is started, the three dimensional model of the piston, or other target object, is made by the geometry calculating unit 21 based on three dimensional data supplied through the input device 1. The model of the targe object is then divided into mesh or cells for FEM analysis (Step S1). Subsequently, conditions of a thermal boundary are set via the input device 1 (Step S2).

The heat transfer coefficients corresponding to the thermal boundary conditions such as heat input from the head lining 52 of the piston 51, heat output from the piston ring 53, heat output from the interior of the piston 51, heat output from the exterior of the piston 51, heat output from the interior of the piston pin 55, and heat output from the end of the connecting rod (con-rod) 56 are determined at the input device 1 as initial conditions, e.g., as shown schematically in FIG. 3. In FIG. 3, a piston pin boss 54 through which the piston pin 55 is inserted is provided as shown.

In an actual internal combustion engine, heat is generated by combustion gases, and generated heat is discharged via the components such as the piston 51, the piston pin 55, the con-rod 56, and the cylinder that is not shown in the figure, and is finally discharged through cooling water, oil, and the remaining components and environment. The input and output of heat is expressed as parameters and analyzed as described above since this phenomenon cannot be simulated completely. In the embodiment of the present invention, the heat transfer coefficients are used as parameters of heat input/output.

As shown in FIG. 4, an example in which the heat transfer coefficients as parameters at the respective parts include seven heat transfer coefficients. The heat transfer coefficients, including the heat transfer coefficient P1 of the head lining 52 of the piston 51, the heat transfer coefficient P2 of the side surface of the piston 51, the heat transfer coefficient P3 of the top ring 53-1, the heat transfer coefficient P4 of a second ring 53-2, the heat transfer coefficient P5 of an oil ring 53-3, the heat transfer coefficient P6 of the inner surface of the piston 51, and the heat transfer coefficient P7 of the piston pin 55, will now be described hereinafter.

The seven heat transfer coefficients including the heat transfer coefficient P1 of the piston head lining 52, the heat transfer coefficient P2 of the side surface of the piston 51, the heat transfer coefficient P3 of the top ring 53-1, the heat transfer coefficient P4 of the second ring 53-2, the heat transfer coefficient P5 of the oil ring 53-3, the heat transfer coefficient P6 of the inner surface of the piston 51, and the heat transfer coefficient P7 of the piston pin 55 are set as the initial conditions.

Subsequently, target temperatures at predetermined specific points on the cross section of the piston 51 shown by dots in FIG. 5 are determined. The target temperatures are target temperatures at the specific points, which are respective strength-focused sampling points for obtaining a piston 51 having a desired strength and thermal characteristics. These target temperatures are also set as initial conditions via the input device 1 together with the heat transfer coefficients P1–P7 in the step S2 in advance.

Subsequent to the determination of the initial conditions, the heat transfer coefficients P1–P7 determined as the initial conditions are read in (Step S3). The target geometry is also read in, e.g., the target temperatures of the predetermined specific points on the locations throughout the piston 51 (Step S4). Then, the response surface is determined by the temperature distribution calculating unit 22 based on a response surface method using the heat transfer coefficients P1–P7 (Step S5).

A method of making a response surface model in Step S5 will now be described. If the seven heat transfer coefficients P1–P7 as parameters are estimated variables, and two quadratic polynomials are employed as response functions, the response surface formula is expressed by the following expression (1) based on the response surface method.

EQUATION (1)

In this Equation (1), ao, bi, cj, dk are unknown values respectively, and the response surface is determined by varying the thermal transfer coefficients P1–P7 several time in a prescribed range. For example, in the range between (0.1–1.0), the response surface is obtained by establishing more than seven equations based on the result of the variation. The seven equations are then solved out of these models (obtained when applied to Equation (1)) as simultaneous equations to obtain the heat transfer coefficients P1–P7.

With respect to Step S5, benchmarks for the respective heat transfer coefficients P1–P7 (each parameter) are determined as shown in FIG. 7 (Step S51). In a case in which each parameter is classified in two benchmarks as an example, as shown in FIG. 8, all the benchmarks of the respective parameters can be adjusted to the benchmark 2 and allocated to the L8 orthogonal table as shown for example in Table 1 below.

TABLE 1

| | Heat transfer coefficients | | | | | | |
|---|---|---|---|---|---|---|---|
| No. | $P_1$ piston head lining | $P_2$ side surface | $P_3$ top ring | $P_4$ second ring | $P_5$ oil ring | $P_6$ inside | $P_7$ piston pin |
| 1 | 1 | 1 | 1 | 1 | 1 | 1 | 1 |
| 2 | 1 | 1 | 1 | 2 | 2 | 2 | 2 |
| 3 | 1 | 2 | 2 | 1 | 1 | 2 | 2 |
| 4 | 1 | 2 | 2 | 2 | 2 | 1 | 1 |
| 5 | 2 | 1 | 2 | 1 | 2 | 1 | 2 |
| 6 | 2 | 1 | 2 | 2 | 1 | 2 | 1 |
| 7 | 2 | 2 | 1 | 1 | 2 | 2 | 1 |
| 8 | 2 | 2 | 1 | 2 | 1 | 1 | 2 |

Based on the benchmarks allocated in the orthogonal table, N iterations of analyses are set to allow contributions of the thermal transfer coefficients P1–P7 to be equal (Step S52). Subsequent to Step S52, preset N iterations of analyses are made (Step S53), and a response surface is produced based on the results of analyses using the method of least squares or the like (Step S55).

The heat transfer coefficients P1–P7 are determined from the response surface model produced in the Step S55 (Step S6) so that the temperatures at the specific points correspond to the target temperatures. The temperature distribution of the piston 51 as a target region can be obtained by conducting heat transfer analysis using the heat transfer coefficients P1–P7 (Step S7).

Temperature distribution of the target region calculated in the Step S7 is as shown schematically by the broken line in FIG. 5. More specifically, it is represented by a dark-light colored figure. FIG. 5 is a cross sectional view of the piston 51 taken in the direction orthogonal to the piston pin 55. Chain double-dashed lines represent the position of the piston pin boss 54. FIG. 6 is also a cross sectional view of the piston 51 taken along the line orthogonal to FIG. 5 showing only the left side of the piston 51 with respect to the centerline thereof. The chain double-dashed lines represent the position of the centerline of the piston pin boss 54.

The temperatures at the specific points are calculated by the specific point temperature calculating unit 23 from temperature distributions obtained in Step S7 (Step S8). The difference $\Delta T$ between the calculated temperatures at the specific points and the target temperatures of the corresponding specific points are obtained by the difference calculating/determining unit 24 (Step S9). Whether or not the differences $\Delta T$ obtained in the step S9 fall within the predetermined prescribed range is checked by the difference calculating/determining unit 24 (Step S10).

In step S10, when the differences $\Delta T$ obtained in the step S9 are determined to be out of the predetermined range, the response surface model is updated by the heat transfer coefficient updating unit 25 based on the results of analyses already obtained and the result of analysis obtained in Step S8 (Step S11). The procedure is performed from Step S6 again.

When the differences $\Delta T$ are determined to have fallen within the predetermined prescribed range, the heat transfer coefficients P1–P7 at the timing when the differences $\Delta T$ have fallen within the predetermined prescribed range are determined to be the heat transfer coefficients of the piston 51, whereby temperature distribution of the piston 51 based on the heat transfer coefficients P1–P7 is obtained.

An example of a state in which the heat transfer coefficients P1–P7 (absolute values) were varied by repeating the steps from Step S6 to Step S11 described above is shown in FIG. 8. An example of a state in which the heat transfer coefficients P1–P7 were converged into the target values (value when the differences $\Delta T$ are converged) is shown in FIG. 9. An example of a state in which the difference $\Delta T$ was converging is shown in FIG. 10. In this example, the differences $\Delta T$ fell within the prescribed range by repeating the steps five times, and was converged into the prescribed preset target temperature range in one-fifth the time period required for the conventional method.

In FIG. 10, a state in which the differences $\Delta T$ at the center portion of the oil ring, at the center portion of the second ring, the center portion of the top ring, the lenten portion of the piston head lining (a), at the center of the upper portion of the piston head lining (b), at the center of the lower portion of the piston (c), at the center portion of the rib (d), at the upper portion of the inside of the chamfer of the piston pin boss (e), at the upper portion of the oil groove inside the chamfer of the piston pin boss (f), and at the lower portion of the inside of the chamfer of the piston pin boss (g) are converged is shown.

In FIG. 11(a), which is a cross sectional view of the piston 51 taken along the direction orthogonal to the piston pin 55, and in FIG. 11(b), which is a schematic drawing of the piston 51 viewed from the bottom of FIG. 11(a), the lenten portion of the piston head lining (a), the center of the upper portion of the piston head lining (b), the center of the lower portion of the piston head lining (c), the center portion of the rib (d), the upper portion of the inside of the chamfer of the piston pin boss (e), the upper portion of the oil groove inside the chamfer of the piston pin boss (f), and the lower portion of the inside of the chamfer of the piston pin boss (g) except for the center portion of the oil ring, the center portion of the second ring, and the center portion of the top ring are designated in the same reference signs as (a)–(g) in FIG. 10 respectively.

In FIGS. 11(a) and (b), an oil groove 9 communicates the inner peripheral side with the outer peripheral side of the piston, and a rib 60 connects the piston pin boss 54 and the outer peripheral wall of the piston. The reference sign "a" designates the portion of the backside of the head lining of the piston that has been reduced in thickness for reducing the weight of the piston.

With the thermal analysis apparatus 10, the optimal heat transfer coefficients can be obtained from the history of variations in temperatures at strength-focused points with respect to the target temperatures at the strength-focused points. Thus, temperature distribution on the target object based on the optimal heat transfer coefficients can be obtained quickly and accurately.

Even if the measured temperatures at the strength-focused points are required, it is not necessarily possible to measure the temperatures at the strength-focused points. Therefore, with the thermal analysis apparatus 10, only one-fifth to one-tenth the time period is necessary in comparison with the case of measuring the temperatures around the focused points and repeating calculations while changing the heat transfer coefficients so as to correspond to measured data in order to estimate temperature distribution based on the measured results.

The method and apparatus for thermal analysis according to the present invention provide several other advantages over the previous attempts of the background art. Since heat transfer coefficients are obtained by automatic repetitive computation, it is not necessary to select the experimental formula, and thus the heat transfer coefficients can be effectively obtained. In addition, since the time period until the differences are converged to obtain accurate parameters is shorter with the present invention, the operating efficiency may also be improved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for thermal analysis having an execution process in which a target region on a piston in an internal combustion engine is divided by dividing a geometric model of the piston into a finite number of finite elements or cells and then the thermal analysis is conducted on the target region using the results of the division of the target region, said execution process comprising the steps of:

obtaining a temperature distribution in the piston using heat transfer coefficients obtained at a plurality of positions on a surface of the target model that is divided into target regions in a first step;

obtaining at least one temperature of a specific paint in the target regions based on the previously obtained temperature distribution in a second step;

calculating differences between the at least one temperature at the specific point and at least one corresponding and predetermined target temperatures at the specific point in a third step;

determining if the calculated differences fall within a prescribed range in fourth step; and changing the heat transfer coefficients of the first step into updated heat transfer coefficients when the differences are determined to be outside of the prescribed range in a fifth step.

2. A method for thermal analysis having an execution process in which a target region on a target object is divided by dividing a geometric model of the target object of the thermal analysis into a finite number of finite elements or cells and then the thermal analysis is conducted on the target region using the results of the division of the target region, said execution process comprising the steps of:

obtaining a temperature distribution in the target object using heat transfer coefficients obtained at a plurality of positions on a surface of the target model that is divided into target regions in a first step;

obtaining at least one temperature of a specific point in the target regions based on the previously obtained temperature distribution in a second step;

calculating differences between the at least one temperature at the specific point and at least one corresponding and predetermined target temperatures at the specific point in a third step;

determining if the calculated differences fall within a prescribed range in a fourth step; and changing the heat transfer coefficients of the first step into undated heat transfer coefficients when the differences are determined to be outside of the prescribed range in a fifth step; wherein the heat transfer coefficients used in the first step are updated with the updated heat transfer coefficients of the fifth step and said first through said fifth steps are repeated until the calculated differences fall within the prescribed range.

3. The method for thermal analysis according to claim 2, wherein the first step further comprises the steps of:

assigning the heat transfer coefficient as an estimated variable; and establishing a simultaneous equation with a plurality of approximate expressions obtained by modifying the heat transfer coefficient within a prescribed range.

4. The method according to claim 3, further comprising the steps of calculating the simultaneous equation for obtaining a response surface and using the response surface as a temperature distribution of the target object.

5. The method according to claim 4, wherein the simultaneous equation is defined in terms of a plurality of thermal transfer coefficients (P1, P2, . . . P7) and a plurality of unknown variables (ao, bi, cj, dk).

6. The method according to claim 5, wherein the simultaneous equation for each heat transfer coefficient and a respective sampling point is defined by:

$$y = f(P_1, P_2, \cdots, P_7)$$
$$= a_0 + \sum_{i=1}^{7} b_i P_i + \sum_{j=1}^{7} c_j P_j^2 + \sum_{k=1}^{6} d_k P_k \cdot P_{k+1}.$$

7. The method according to claim 6, wherein the target object is a piston in an internal combustion engine.

8. The method according to claim 2, wherein the target object is a piston in an internal combustion engine.

9. A thermal analysis apparatus for performing a thermal analysis process, said apparatus comprising:

means for dividing a target region on a target object by dividing a geometric model of the target object of the thermal analysis process into a finite number of finite elements or cells and conducting thermal analysis on the target region using the results of the division of the target region;

means for obtaining a temperature distribution in the target object using first heat transfer coefficients obtained at a plurality of positions on a surface of the target model that is divided into target regions;

means for obtaining at least one temperature of a specific point in the target regions based on the previously obtained temperature distribution;

means for calculating differences between the at least one temperature at the specific point and at least one corresponding and predetermined target temperatures at the specific point;

means for determining if the calculated differences fall within a prescribed range; and means for changing the first heat transfer coefficients into undated heat transfer coefficients when the differences are determined to be outside of the prescribed range;

wherein said means for obtaining a temperature distribution in the target object includes means for assigning the heat transfer coefficient as an estimated variable; and means for establishing a simultaneous equation with a plurality of approximate expressions obtained by modifying the heat transfer coefficient within a prescribed range.

10. The thermal analysis apparatus according to claim 9, wherein said means for establishing a simultaneous equation includes a section for calculating the simultaneous equation for obtaining a response surface and using the response surface as a temperature distribution of the target object.

11. The thermal analysis apparatus according to claim 10, wherein the simultaneous equation is defined in terms of a plurality of thermal transfer coefficients (P1, P2, ... P7) and a plurality of unknown variables (ao, bi, cj, dk).

12. The thermal analysis apparatus according to claim 11, wherein the simultaneous equation for each heat transfer coefficient and a respective sampling point is defined by:

$$y = f(P_1, P_2, \cdots, P_7)$$
$$= a_0 + \sum_{i=1}^{7} b_i P_i + \sum_{j=1}^{7} c_j P_j^2 + \sum_{k=1}^{6} d_k P_k \cdot P_{k+1}.$$

\* \* \* \* \*